United States Patent [19]

Szegvary

[11] Patent Number: 4,759,714

[45] Date of Patent: Jul. 26, 1988

[54] TOOTH ROOT CHANNEL ANCHOR

[76] Inventor: Georg Szegvary, Buchholz-Strasse 39, 8053 Zürich, Switzerland

[21] Appl. No.: 269,982

[22] Filed: Jun. 3, 1981

[30] Foreign Application Priority Data

Jun. 26, 1980 [CH] Switzerland ............... 4896/80

[51] Int. Cl.⁴ .................................................. A61C 5/08
[52] U.S. Cl. ..................................................... 433/221
[58] Field of Search ........................ 433/220, 221, 174

[56] References Cited

U.S. PATENT DOCUMENTS

| | | | |
|---|---|---|---|
| 1,479,508 | 1/1924 | Maeulen et al. | 433/221 |
| 2,609,604 | 9/1952 | Sprague | 433/174 |
| 2,705,837 | 4/1955 | Gerlach | 433/221 |
| 3,589,011 | 6/1971 | Sneer | 433/174 |

FOREIGN PATENT DOCUMENTS 562605 3/1974 Switzerland ............... 433/220

Primary Examiner—Robert Peshock
Attorney, Agent, or Firm—Marks, Murase & White

[57] ABSTRACT

A tooth root channel anchor comprising a conical anchoring member, said anchoring member including a head portion upon which an artificial tooth can be built up, the anchoring member having a conicity or taper of from about 1° to about 5° and having a longitudinal axis and a periphery, a plurality of anchoring ribs disposed around said periphery of said anchoring member and at least two grooves formed in said anchoring member extending parallel to said longitudinal axis, said grooves acting as cutting and cement discharging grooves.

5 Claims, 1 Drawing Sheet

TOOTH ROOT CHANNEL ANCHOR

FIELD OF THE INVENTION

The present invention relates to a tooth root channel anchor having an anchoring member and a head portion on which an artificial tooth may be built up.

DISCUSSION OF PRIOR ART

An anchor of this general type is described in German Pat. No. 1,541,209 wherein the anchoring member is cylindrical and the head portion is hexagonal. Such a cylindrical anchoring member does not provide optimum securing, and there is a risk that it will work loose. On the other hand, anchors are known having securing members which are screw-threaded and which are mounted by being screwed into the root channel. In such a case, there is a risk that the root channel will fracture during the insertion operation as a result of the relatively large angle of taper of the securing member.

BACKGROUND OF THE INVENTION

The present invention seeks to provide a tooth root channel anchor which ensures secure attachment without the risk that the root channel will fracture while it is being inserted; but which is detachable at any time, if desired.

SUMMARY OF THE INVENTION

According to the present invention, there is provided a tooth root channel anchor comprising a conical anchoring member, the anchoring member including a head portion upon which an artificial tooth can be built up, the anchoring member having a conicity or taper of between approximately 1° and 5° and having a longitudinal axis and a periphery, a plurality of anchoring ribs disposed around said periphery of said anchoring member and at least two grooves formed in said anchoring member extending parallel to the longitudinal axis, said grooves acting as cutting and cement discharging grooves.

BRIEF DESCRIPTION OF THE DRAWINGS

The invention will be described more fully hereinafter, by way of example, with reference to the accompanying drawings, in which.

DESCRIPTION OF PREFERRED EMBODIMENTS

Figure 1:
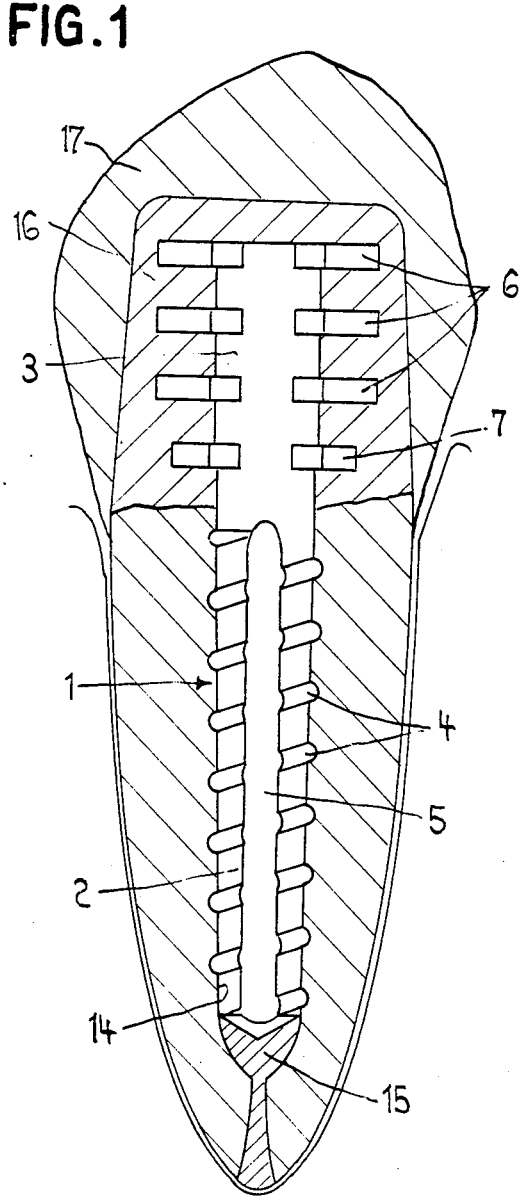
FIG. 1 shows a schematic vertical section through a first embodiment of an anchor in accordance with the present invention, the anchor being secured in a tooth.

In FIG. 1 there is shown an anchor 1 comprising an anchoring member 2 and a head portion 3. The anchoring member 2 is tapered slightly towards the end remote from the head portion 3 and has a conicity of 2°. The member 2 is provided with anchoring ribs 4 around its periphery. These ribs 4 have an incline of substantially 70° relative to the longitudinal axis of the member 2 and are rounded off so as to ensure maximum displacement.

Figure 2:
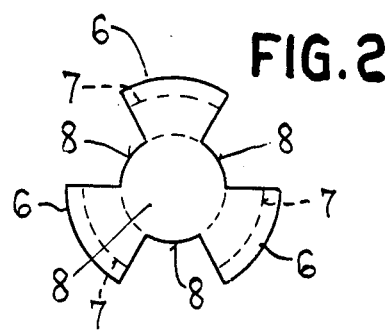
FIG. 2 is an end view through a head portion of the anchor shown in FIG. 1.
Figure 3:
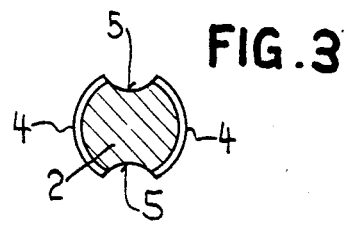
FIG. 3 is a cross-sectional view through the anchoring member forming part of the anchor shown in FIG. 1.

The anchoring member 2 is provided with two longitudinally extending cutting grooves 5 (best seen in FIG. 3) which simultaneously serve as cement discharging grooves. These cutting grooves enable the anchor to be inserted into the root channel without the use of excessive force. It is therefore unnecessary to ram the anchor into the channel, whereby the risk of the root channel fracturing is obviated or at least minimized. The height of the anchoring ribs is substantially 0.1 mm. The head portion 3 is provided with four layers of vanes 6, 7 the upper three layers of vanes 6 have a larger diameter than the lowermost layer 7. As shown in FIG. 2, the head portion 3 is provided with three longitudinally extending grooves 8.

Figure 4:
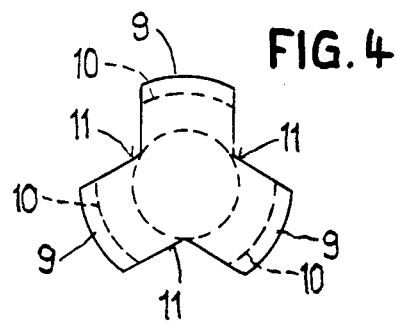
FIGS. 4 and 5 are cross-sectional views similar to FIGS. 2 and 3 respectively of a second embodiment of an anchor in accordance with the present invention.
Figure 5:
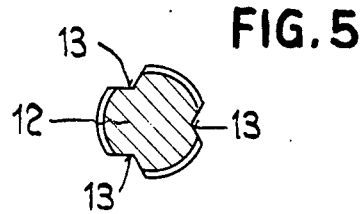

However, as can be seen in FIG. 4, the vanes, here referenced 9 and 10 may be provided with different shapes. By doing so, the three longitudinal grooves 11, corresponding to the grooves 8 in FIG. 2, may have a substantially V-shaped profile. It will be seen in FIG. 5 that the anchoring member, now referenced 12, may also have three substantially V-shaped cutting grooves 13.

The securing of the anchor and the build-up of an artificial tooth thereon will now be described with reference to FIG. 1. A root channel 14 is initially prepared, by the use of suitable instruments so that it corresponds to the shape of the anchoring member. ISO instruments are suitable for this purpose. The channel is sealed in a downward direction by means of a known root filler 14. It should, however, be pointed out that the shape and diameter of the drilled-out root channel should correspond to the shape and the diameter of the anchoring member excluding the ribs. A specific quantity of suitable cement or similar material is subsequently inserted into the channel and the anchor is introduced therein. The anchoring member is then secured by rotating through an angle of, for example 90° but not more than 360°, whereby the securing ribs displace a portion of the cement and provide a bayonet-type locking arrangement. Since the ribs produce a permanent attachment only in one specific, small angular region, this connection may be loosened at any time without damaging the root channel or the remaining tooth root. A conventional build-up material 16 is subsequently applied around the head portion 3, which acts as a reinforcement member, and a tooth crown 17 may then be mounted on this material.

A corrosion-resistant alloy may be used as material for the anchor. In such a case, the anchoring member may be provided with more than two or three grooves, while the head portion need not necessarily be provided with four layers of vanes. Fewer or more vanes may be provided. Similarly, two or four longitudinally extending grooves may be provided instead of three as described hereinbefore. The conicity or taper of the anchoring member need not be exactly 2° and may be between 1° and a maximum of 5°. The angle of inclination of the ribs 4 relative to the longitudinal axis of the anchoring may vary within the range of 70° to 80° and the rib height may be up to 0.15 mm.

I claim:

1. An improved tooth root channel anchor of the type having a head portion for attachment of an artificial tooth thereto and an anchoring member portion for attachment to a tooth root channel, wherein the improvement comprises:

said anchoring member having a longitudinal axis; a radially-decreasing conical axial profile along said axis of between approximately two degrees and five degrees, said profile decreasing from a portion proximate said head to a distal end portion; said distal end having a rounded profile; a helically wound anchoring rib attached to and protruding from the entire length of said anchoring member about said longitudinal axis, and having a wound pitch of between approximately seventy degrees and eighty degrees relative said axis; and said anchoring member defining two or more longitudinal groove means parallel to said longitudinal axis for cutting said rib in a self-threading fashion into the wall of a hole defined in said root channel in order to attach said anchoring member to a root channel during a dental attachment procedure and for discharging excess dental cement that may be present in a root channel hole during a dental attachment procedure.

2. The improved anchor as recited in claim 1, wherein said conical profile of said anchoring member is approximately 2°.

3. The improved anchor as recited in claim 1, wherein said rib protrudes from said anchoring member between approximately 0.10 mm. and 0.15 mm.

4. The improved anchor as recited in claim 1, wherein said head portion has a longitudinal axis substantially co-axial with said longitudnal axis of said anchoring member and a periphery, said periphery defining three groves formed therein extending parallel to said longitudinal axis of said head portion, said periphery also having four layers of vanes extending substantially perpendicularly to said longitudinal axis and being outwardly directed from said longitudinal axis, said layers of vanes extending substantially parallel to one another, said layer of vanes nearest said anchoring member having a smaller diameter than said remaining layers of vanes.

5. The improved anchor as recited in claim 4, wherein said grooves formed in said head portion and said grooves formed in said anchoring member are each substantially V-shaped.

* * * * *